United States Patent [19]
Michler et al.

[11] Patent Number: 5,354,943
[45] Date of Patent: Oct. 11, 1994

[54] METHODS OF HIGH FREQUENCY TISSUE REGENERATION, REGENERATION OF HERBICIDE-TOLERANT POPULUS PLANTS THEREWITH, AND THE HERBICIDE-TOLERANT PLANTS MADE THEREBY

[75] Inventors: Charles H. Michler; Bruce E. Haissig, both of Rhinelander, Wis.

[73] Assignee: The United States of America as represented by the Secretary of the Agriculture, Washington, D.C.

[21] Appl. No.: 711,610

[22] Filed: Jun. 7, 1991

Related U.S. Application Data

[63] Continuation of Ser. No. 447,458, Dec. 7, 1989, abandoned, which is a continuation-in-part of Ser. No. 192,408, May 4, 1988, abandoned.

[51] Int. Cl.$^5$ .......................... A01H 5/00; A01H 4/00; A01H 1/00
[52] U.S. Cl. .......................... 800/230; 800/DIG. 48; 435/172.1; 435/240.4; 435/240.45; 435/240.49
[58] Field of Search .............. 435/172.1, 172.3, 240.4, 435/240.45, 240.49, 240.50; 47/58, 58.03, 58.05; 800/200, 205, 230, DIG. 49

[56] References Cited

U.S. PATENT DOCUMENTS

| | | | |
|---|---|---|---|
| 4,443,971 | 4/1980 | Chaleff | 47/58 |
| 4,774,381 | 9/1988 | Chaleff | 800/1 |
| 4,795,855 | 1/1989 | Fileffi et al. | 800/1 |

OTHER PUBLICATIONS

Zaerr et al., (1985), In Tissue Culture in Forestry, Ed. Bonga and Durzar Marfinis M. J. Hoff, Dr. W. Junk, Dordracht, pp. 231–255.
Michler et al., (1987), Proc. IUFRO Working Party S2. 04–07, Grosshansdorf, W. Germany, Ed., Ahyia, (1988), pp. 183–189 (Abstract).
Akinyemija et al., (1982), Can. J. Forest Research, 12(3):708–712.
Ahiya, (1986), Phy., *Handbook of Plant Cell Culture*, vol. 4, pp. 626–651, Ed., Evans et al., MacMillan.
Lester et al., (1977), Forest Science, 23(1):122–131.
J. J. Fillatti, J. Sellmer, B. McCown, B. Hassig, and L. Comai, "*Agrobacterium Mediated Transformation and Regeneration of Populus*", Mol. Gen. Genet., 206:192–199 (1987).
J. C. Sellmer, B. H. McCown and B. E. Haissig, "Shoot culture dynamics of six Populus clones", Tree Physiology 5, 219–227 (1989).
B. H. McCown, "From gene manipulation to forest establishment: shoot cultures of woody plants can be a central tool", Tappi Journal 68(5):116–119 (May 1985).
R. H. Zimmerman, "Regeneration in Woody Ornamentals and Fruit Trees", Cell Culture and Somatic Cell Genetics of Plants (Indra K. Vasil Ed.) vol. 3, Chapter 12, pp. 243–258 (1986).

(List continued on next page.)

*Primary Examiner*—Gary Benzion
*Attorney, Agent, or Firm*—M. Howard Silverstein; John D. Fado

[57] ABSTRACT

Methods of in vitro culturing of tree tissue are disclosed in which high frequency tissue regeneration is achieved thereby increasing the likelihood of regenerating somaclonal variants having desirable traits. These methods include: culturing with a ratio of naphthaleneacetic acid and benzyladenine, or of benzyladenine and zeatin, in a tissue regeneration medium, the ratio being selected to induce a high frequency of tissue regeneration; culturing on a tissue regeneration medium having a high auxin concentration with a relatively low cytokinin concentration for a short period of time, e.g. up to ten days, to regenerate a high number of morphogenic callus cells; and, regenerating somatic embyros using a medium comprising 2,4-dichlorophenoxyacetic acid, benzyladenine, sucrose and glutamine, for high frequency regeneration of emboyogenic calli which are then developed into somatic embryos. These high frequency tissue regeneration methods are used to develop plants having tolerance to toxic chemicals by combining the methods with in vitro exposure to toxic chemical thereby to challenge somaclonal variants with the toxic chemical to test for and recover tolerant variants.

23 Claims, 1 Drawing Sheet

OTHER PUBLICATIONS

A. D. Krikorian "Plant tissue culture: Preceptions and Realities", Proc. Indian Acad. Sci. (Plant Sci) 98(6):425–464 (Dec. 1988).

S. Garton et al., "Biotechnology and Genetic Optimization of Fast-Growing Hardwoods" (Final Report to the New York State Energy Research and Development Authority) (1989).

E. F. George and P. D. Sherrington, "Plant Propagation by Tissue Culture", pp. 44–48, 289, 307–308, 330, 347–348 and 358–360 (1984).

G. S. Cheema, "Somatic embryogenesis and plant regeneration from cell suspension and tissue cultures of mature himalayan poplar (*Populus ciliata*)", Plant Cell Reports 8:124–127 (1989).

P. Krogstrup, "Effect of culture densities on cell proliferation and regeneration from embryogenic cell suspensions of *Picea sitchensis*", Plant Science 72:115–123 (1990).

T. Powledge, "Biotechnology Touches the Forest", Biotechnology 2:763–772 (Sep. 1984).

B. Haissig, N. Nelson and G. Kidd, "Trends in the Use of Tissue Culture in Forest Improvement", Biotechnology 5:52–59 (Jan. 1987).

P. Gupta and D. Durzan, "Biotechnology of Somatic Polyembryogenesis and Plantlet Regeneration in Loblolly Pine", Biotechnology 5:147–151 (Feb. 1987).

E. Bauer and C. Michler, "Microspray Applicator and Enclosure for Administering Chemicals to Plants", HortScience 24(4):704 (Aug. 1989).

C. Michler and E. Bauer, "Somatic Embryogenesis in Plant Cell Cultures of *Populus*", IN VITRO cellular & developmental biology 23(3) (Part II):46A (Abstract 140) (Mar. 1987).

C. Michler and E. Bauer, "Selection of Somaclonal Variants for Herbicide Tolerance in Tissue Cultured Plantlets of Populus", IN VITRO cellular & developmental biology 23(3) (Part II):47A (Abstract 141) (Mar. 1987).

C. Michler and E. Bauer, "Somaclonal Variants of Poplar that Tolerate Sulfometron Methyl", IN VITRO cellular & developmental biology 24(3) (Part II): 52A (Abstract 164) (Mar. 1988).

C. Michler and E. Bauer, "Selection for Herbicide Tolerance in *Populus* to Sulfometuron Methyl In Vitro", Genetic Manipulation of Woody Plants 479 (J. Hanover and D. Keathley Eds. 1988).

METHODS OF HIGH FREQUENCY TISSUE REGENERATION, REGENERATION OF HERBICIDE-TOLERANT POPULUS PLANTS THEREWITH, AND THE HERBICIDE-TOLERANT PLANTS MADE THEREBY

This application is a continuation of application Ser. No. 07/447,458, filed Dec. 7, 1989, now abandoned, which is a continuation-in-part of application Ser. No. 07/192,408, filed May 4, 1988, now abandoned.

BACKGROUND OF THE INVENTION

This invention relates to in vitro culturing processes for regenerating tissue, e.g. shoots, somatic embryos or roots, of tree genotypes at high frequency, to the use of such processes for producing tree genotypes which tolerate normally lethal dosages of toxic chemicals, such as herbicides, and to the tolerant tree genotypes thus produced.

Trees are being increasingly exposed to chemical stress because of urbanization, industrialization, and intensive forest and horticultural management practices. Chemical stress is produced by such chemicals as sulfur dioxide, ozone, nitrogen oxides, mineral salts, heavy metals, and acid precipitation. Chemical stress can damage or kill trees.

Herbicides are another cause of chemical stress to trees. Yet, the use of herbicides is desirable in tree cultivation for preparing planting sites, reducing weed competition, converting sites in order to plant other species, and additional purposes. As tree cultivation intensifies, herbicide use is increasing in order to make production more economical. Cultivation with herbicides is less expensive than mechanical methods which may not even work.

Herbicides could be used more and their use would be mere efficient if the tree crops exposed thereto are tolerant of the herbicides. This is particularly so in the case of the genus Populus, a genus of great value to the forest industry, trees of this genus being the object of much use in short rotation intensive culture to yield pulp, fiberboard and fuelwood. Unfortunately, Populus trees are sensitive to many herbicides. Naturally occurring Populus trees do not have commercially useful levels of tolerance to such environmentally safe, broad-spectrum herbicides as glyphosate, sulfonylureas (sulfometuron methyl), or imidazolinones. In the absence of herbicides, weed competition limits the plantation establishment of Populus trees even though the weeds can be killed by such herbicides. Present Populus weed control methods involve labor-intensive shielding methods or are limited to use during cessation of the growth of the Populus crop.

Chemical stress tolerance and other traits are difficult or impossible to obtain in trees by traditional crossbreeding. If higher plant genes for such traits exist, they occur at such low frequencies in tree populations that they cannot be economically selected, if at all. As a result, it is difficult or impossible to obtain tolerant parents for breeding. In addition, trees take a long time to reach sexual maturity, usually many years. Thus, traditional breeding for a trait, such as chemical stress tolerance, would take years, perhaps a century. Additionally, often nothing is known about the modes of inheritance of a trait in trees. This lack of knowledge further complicates breeding.

In vitro tissue culturing offers a practical alternative for developing genetically modified individuals of tree species. Variants can be produced during in vitro culture propagation whereby all the progeny of a given plant material are not identical. This variation resulting solely from the in vitro culturing process is known as somaclonal variation. Somaclonal variation may be Mendelian (quantitative) and non-Mendelian (qualitative), and may arise from preexisting cellular genetic variation or variation arising in the culture process, or both. Somaclonal variants may be expressed, described, and tested from a single passage in microculture and may have desirable economic traits that can be exploited directly through their sexually or vegetatively propagated progenies, or indirectly by further somaclonal or traditional breeding programs.

SUMMARY OF THE INVENTION

An object of the invention is to provide processes for in vitro culturing of tree tissue which achieve a high frequency of tissue regeneration from explants capable of generating adventitious or axillary buds in culture. The higher the frequency and consequent number of regenerations, e.g. the rate of adventitious bud formation and shoot or root multiplication, the greater the possibility of regenerating somaclonal variants.

An object of the invention is to provide high frequency in vitro tissue regeneration processes for production of somaclonal variants which processes are much more rapid in time compared with traditional tree breeding techniques thus making possible the development of traits difficult or impossible to obtain by traditional crossbreeding.

Another object is to provide high frequency in vitro tissue regeneration processes capable of regenerating adventitious tissue from many different cell sources within a plant, including cells from plant parts not usually likely to create a new plant.

A further object of the invention is to provide in vitro culture processes combining high frequency tissue regeneration with in vitro exposure to toxic chemical thereby to challenge any regenerated somaclonal variants with the chemical, in order to test for and recover tree variants tolerant of the normally toxic chemical.

Another object of the invention is the production of new genotypes of the Populus genus tolerant of chemicals, e.g. herbicides, toxic to their parent genotypes.

These and other objects are achieved by in vitro culture processes involving auxin pulsing or somatic embryogenesis, in vitro culture processes combining auxin pulsing or somatic embryogenesis with exposure to toxic chemical, and an in vitro culture process involving the combination of tissue regeneration using a maximized ratio of plant growth regulating hormones with exposure to toxic chemical.

In the process maximizing the ratio of growth regulators, plant tissue is initially cultured on a medium having a specific ratio of naphthaleneacetic acid (NAA) and benzyladenine (BA), or a specific ratio of BA and zeatin, while contacting the tissue with a toxic chemical for which tolerance is to be developed. The ratio is maximized to induce a high frequency of tissue regeneration. Then, the plant tissue is subsequently subcultured on tissue regeneration medium in the presence of the toxic chemical for a total period of time that insures necrosis of any non-tolerant tissue and that any surviving tissue has developed tolerance to the chemical. The concentration of the toxic chemical during this subsequent subculturing is at least as high as the concentration which is 100% lethal to normal, non-tolerant plants. Intermediate subculturing free of toxic chemical may be conducted between the initial culturing and the subsequent subculturing in order to select regenerants that can continue to survive recurrent exposure to herbicide and to shorten the time required for the overall process by regenerating plant tissue more quickly.

In the auxin pulsing process of the invention, high frequency tissue regeneration is achieved by culturing plant tissue in darkness on a tissue regeneration medium having a high auxin concentration with a relatively low cytokinin concentration for regenerating a high number of morphogenic callus cells, followed by subculturing on tissue regenerating medium thus resulting in a high frequency of tissue regeneration and an increased possibility of somaclonal variants. The high auxin culture is conducted for only a short time period in order to promote the high frequency of morphogenic callus regeneration, but to avoid the initiation of root regeneration which commences therafter, unless root formation is the desired result. The process may include two high auxin concentration cultures each for a short time length, a culture with a high auxin concentration preceded by a preliminary culture with a higher auxin concentration, tissue from the preliminary culture being subcultured in the high auxin culture. Auxin pulsing is used in the development of tolerance to toxic chemicals by taking tissue from the high auxin culture and further subculturing the tissue while contacting it with the toxic chemical.

In the sometic embryogenesis process of the invention, high frequency tissue regeneration is achieved by culturing plant tissue with a medium comprising 2,4-dichlorophenoxyacetic acid (2,4-D), BA, sucrose and glutamine to form callus cells, and subculturing the callus cells with a medium comprising BA and sucrose, but with 2,4-D eliminated or reduced, to form sometic embryos from the callus cells. The callus cell forming stage may include first culturing the explant on a solid medium having the four specified ingredients followed by subculturing in an agitated liquid medium comprising 2,4-D, BA and sucrose.

Somatic enbryogenesis may be used in the development of tolerance to a toxic chemical by first forming callus cells of a tree genotype in callus forming media in the absence of the toxic chemical followed by subculturing the thus formed callus cells in a median forming further callus cells, this latter medium having therein the toxic chemical at a concentration less than a lethal concentration. Surviving callus cells are furher subcultured with successive callus forming media having increasing concentrations of the toxic chemical until concentrations greater than a lethal level are reached. This subculturing with the toxic chemical is preferably conducted on solid medium.

Also encompassed in the invention are the toxic chemical tolerant trees produced by the foregoing processes, in particular, new trees of the genus Populus which survive an application of either of the toxic herbicides glyphosate or sulfometuron methyl at concentrations equal to or greater than the concentrations lethal to the trees' parent genotypes.

DETAILED DESCRIPTION

Figure 1A:
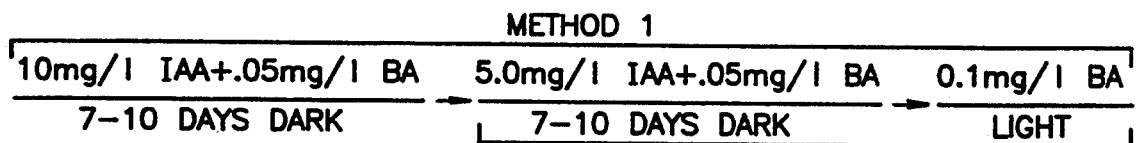
FIG. 1a shows schematically embodiments of the auxin pulsing culture process of the invention as conducted in Example 8.

The culture processes of the invention may be applied to any tree genotypes whose explants are capable of in vitro culture regeneration into whole plants and are capable of the production of somaclonal variants during such regeneration. Trees of the genus Populus, i.e. poplars, aspens and cottonwoods, are usable in the processes of the invention. Specific examples of Populus genotypes to which the processes have been applied are listed in Table 1.

TABLE 1

| Hybrid Clone | Parentage | Section |
|---|---|---|
| NC-5339 | P. alba × P. grandidentata | Leuce |
| NC-5272 | P. nigra × P. laurifolia | Aigeiros and Tacamahaca |
| NC-11390 | P. maximowiczii × P. trichocarpa | Tacamahaca |
| NC-5331 | P. nigra betulifolia × P. trichocarpa | Aigeiros and Tacamahaca |
| NC-5326 | P. deltoides × P. nigra | Aigeiros |

The "NC" designation is the Forest Service North Central Forest Experiment Station accession number.

The explants used to initiate the various cultures of the invention are pieces of living plant tissue taken from a suitable source such as stock cultures maintained specifically for the purpose. The plant tissue may be taken from various plant organs, such as nodal or internodal stems, leaves or roots. It is preferred that the plant tissue be wounded to induce greater callus formation. Therefore, in the preferred embodiments, leaves are used with their apical and basal ends removed to form leaf pieces; or, leaf disks are punched out from leaves with a cork borer. Nodal or internodal stem pieces and severed root tips are also preferred. If rooted shoots are desired, they may be obtained by rooting shoot tips on MS medium after a pre-culture dip in 500 ppm NP-IBA, a compound for stimulating root-generation.

The culture processes of the invention may be used to develop tolerance against any toxic chemical having a damaging effect on a tree genotype's tissue cultures which is similar to the chemical's effect on a whole plant of that genotype, e.g. any metabolic effect which manifests itself identically both at the cellular and at the whole plant levels.

With reference to trees of the Populus genus, the present processes lend themselves to testing for tolerance to modified amino acid herbicides such as glyphosate (ROUNDUP, Monsanto Company), and to sulfonylurea herbicides such as sulfometuron methyl (OUST, DuPont Company) and chlorsulfuron (GLEAN, DuPont Company). The processes may also be used with imidazolinones (American Cyanamid Company) which have a mode of action identical or similar to sulfonylureas, even though the respective compounds are structurally different.

"Tolerance" as used herein refers to the ability to survive exposure to a toxic chemical at concentrations equal to or greater than the concentration (hereinafter: "$LD_{100}$") which is 100% lethal to the normal parent genotype at the same level of development. The concentration that is 100% lethal varies among genotypes. In addition, the $LD_{100}$ for the germplasm of a particular tree may vary as the tissue becomes more highly developed and mature, going from callus to adventitious shoot to rooted shoot to ex vitro rooted plant. The higher the level of plant development, i.e. the more complete and better organized a plant is, the greater is the dosage required to be lethal. This is the case, for example, with sulfometuron methyl when used with Populus germplasm at each stage of plant development. Therefore, a determination of the $LD_{100}$ must be made for each genotype as well as for the stage of plant growth for which tolerance will be tested.

Tissue samples of a tree genotype are analyzed for the 100% lethal dosage level by explanting them on culture plates containing a solidified growth medium. A preferred growth medium comprises basal Murashige and Skoog medium (1962) (hereinafter: "MS") supplemented with 0.1 mg/l BA and 20 g/l sucrose and solidified with 0.6% Difco Bacto agar. The toxic chemical is added to the growth medium in the individual plates before solidification at final concentrations which range from sublethal to lethal. The cultures are then grown in a growth environment for an adequate period of time after which they are analyzed for necrosis.

In the maximized growth regulator ratio process, high frequency regeneration of tissue, e.g. shoots or roots, is achieved with applications of specific maximized ratios of the plant growth regulating hormones naphthaleneacetic acid (NAA) and benzyladenine (BA) or of specific ratios of BA and zeatin. NAA is a synthetic auxin that promotes root initiation, cell division, and cell expansion. BA is a synthetic cytokinin which promotes shoot meristem formation and cell division. The frequency of regeneration is greater with the use of NAA and BA compared with BA and zeatin.

The effect of the growth regulators on the regeneration potential of tree genotypes, i.e. the frequency of regeneration, varies among genotypes. For example, the five Populus clones tested differed in their ability to produce the greatest frequency of adventitious shoots, roots and morphogenic callus in the shortest period of time in response to the growth regulators. Therefore, the maximized ratio of plant growth regulating hormones must be individually determined for each tree genotype by testing each genotype with various combinations of the growth regulators. This is done with factorial experiments. Explants of the tree genotypes to be tested are obtained from continuous shoot or root generating stock cultures or from any other appropriate source. These explants are then cultured on growth medium with varying ratios of the growth regulators. In the preferred embodiment with Populus genotypes, this medium is MS containing 100 mg/l myoinositol, 200 mg/l casein hydrolysate and 20% sucrose, solidified with 0.6% Difco Bacto agar (pH 5.8). Data is taken after an appropriate growing period and the cultures are measured for tissue production, i.e. shoot and/or root production. The specific ratios producing the highest frequency of shoot and/or root regeneration for each genotype are then used as the growth regulator additives for each genotype when culturing in contact with toxic chemical. Frequency of regeneration also varies based on the amount of time of regulator application to the explants and the type of explant used from a genotype. Factorial experiments analogous to those for the growth regulator ratios can be conducted to optimize time of application and explant choice for each genotype.

Having determined the growth regulator ratio which induces the highest frequency of shoot or root regeneration for a genotype, explants from a culture of the genotype are cultured on a medium containing the maximized frequency growth regulator ratio while exposing the explants to the toxic chemical. The explants are exposed by introducing the toxic chemical into the maximized growth culture medium on which tissue is to be grown, although the explants can be otherwise contacted with the chemical, such as by dipping the leaf pieces or shoots in the chemical prior to placing in the high frequency culture medium. However, addition of the toxic chemical as a medium addendum is an efficient technique, better and simpler than dipping. Addition as a medium addendum results in fewer non-tolerant shoots being regenerated and provides an easier way to quantify the amount of toxic chemical applied. By these methods, time explants are exposed to the toxic chemical before they have begun to initiate adventitious shoots or roots.

The explants are cultured in darkness on the high frequency regeneration medium amended with the toxic chemical. A preferred medium is MS containing 100 mg/l myoinositol, 200 mg/l casein hydrolysate and 20% sucrose in addition to the growth regulators and the toxic chemical, and solidified with 0.6% Difco Bacto agar (pH 5.8). This culture induces the formation of a large number of buds. The initial darkness is an advantage with respect to developing glyphosate or sulfometuron methyl tolerance in Populus trees. Since these herbicides affect chlorophyl production which occurs in light, culturing in darkness is believed to reduce the initial stress on the plant tissue thereby aiding in tolerant tissue regeneration.

After the initial culturing and before subsequent subculturing with toxic chemical, one or more intermediate subcultures free of toxic chemical may be conducted in order to regenerate intermediate tissue growth in the absence of the chemical. This intermediate subculturing insures that tissue surviving the subsequent subculturing with the toxic chemical has the ability to continue to survive recurrent exposure to the toxic chemical since temporary tolerance developed during the initial culturing would disappear during the intermediate subculturing. The intermediate subculturing also shortens the overall time needed for the process by accelerating tissue development.

The plant tissue is then further subcultured, also referred to herein as "rechallenged", on tissue regeneration medium in the presence of the toxic chemical sufficiently to insure that any surviving tissue has developed tolerance to the chemical. A sufficient exposure is insured by further subculturing the tissue in the presence of a concentration or concentrations of the chemical for a total period of time necessary to insure necrosis of any non-tolerant tissue.

This further subculturing is conducted with light on a tissue regeneration medium amended with a growth regulator and sucrose. Preferably, the growth regulator is BA. A preferred regeneration medium for the rechallenge is MS containing 100 mg/l myoinositol, 200 mg/l casein hydrolysate, 20 g/l sucrose and 0.1 mg/l BA, solidified with 0.6% Difco Bacto agar (pH 5.8).

Sufficient exposure to the toxic chemical has been provided by one initial culture in darkness of 30 days duration followed by a rechallenge consisting of three 30 day subcultures. The length of the individual cultures and, consequently, of the number of cultures needed, may vary depending on the rate of nutrient consumption and the breakdown of the toxic chemical over the time span of an individual culture.

The concentration of the toxic chemical during the initial culture may be at any toxic chemical concentration greater than, less than, or equal to the $LD_{100}$ concentration. Preferably, the initial toxic chemical concentration is at least equal to the $LD_{100}$ concentration. All the toxic chemical concentrations during the subsequent subculturing are at the $LD_{100}$ concentration or greater. Where the initial toxic chemical concentration is less than or equal to the $LD_{100}$ concentration, the subsequent toxic chemical concentrations are at least at the $LD_{100}$ concentration. Where the initial toxic chemical concentration is equal to or greater than the $LD_{100}$ concentration, the subsequent toxic chemical concentrations may be at the same concentration as the initial concentration.

In one embodiment of the maximized growth regulator ratio process, samples of plant tissue from a tree genotype, i.e. leaf pieces or disks, are initially cultured in darkness on a high frequency regeneration medium supplemented with sucrose and with varying concentrations of a toxic chemical. This initial culture is continued until the medium is substantially exhausted, a period of thirty days. The plant tissue surviving this initial culture in the dark is next subcultured in the light on tissue regeneration medium including a growth regulator but without toxic chemical present. Preferably, the medium is MS with a growth regulator content of 0.1 mg/l BA. The surviving plant tissue is subcultured continuously in this manner until any surviving shoots become greater than 1 cm, which is a shoot size determined to provide shoots suitable for further subculturing in the presence of the toxic chemical. The time period of each subculture is thirty days, by the end of which time the medium is substantially exhausted. Preferably, this intermediate subculturing for shoot regeneration in the absence of the chemical comprises three or four continuous thirty day subcultures. The shoots are then rechallenged with the toxic chemical for a number of subcultures to insure that only tolerant shoots have been regenerated. Preferably, the rechallenge is done by three consecutive subcultures of the shoots each for a thirty day period on shoot regeneration medium with the chemical present at the $LD_{100}$ concentration.

Exposure to the toxic chemical is completed with the completion of the rechallenge. Shoots surviving the rechallenge are then continuously subcultured on shoot regeneration medium with growth regulator until shoots are developed of a size sufficient to insure that the shoots will survive rooting in vitro to form plantlets and planting ex vitro for further growth. The minimum size for shoots chosen for rooting is 2 cm or greater with a size of 3 cm or greater being preferred. The continuous subculturing on shoot regeneration medium after rechallenge is preferably conducted on MS+0.1 mg/l BA medium for three consecutive 30 day subcultures after which any shoots greater than about 3 cm are developed into complete plantlets. Where the plant material surviving rechallenge are roots, appropriate growth regulators for regenerating plantlets from roots are used.

In the auxin pulsing process, plant tissue is first cultured in darkness for a short period of time on a tissue regeneration medium amended with a high auxin concentration in combination with a relatively low cytokinin concentration. The time length of this culture is determined by the frequency of morphogenic callus cell formation, more cells being formed with time, as limited by the need to avoid the initiation of root formation by the morphogenic calli if left in the culture too long, unless root formation is desired. Preferably, the time length of this culture is 7 to 10 days.

This culture is preferably preceded by a short preliminary culture in darkness on a tissue regeneration medium amended with a high auxin concentration in contination with a relatively low cytokinin concentration. The auxin concentration in this preliminary culture is higher than that in the following high auxin culture. The time length of this preliminary culture is determined by the same factors as the following high auxin culture and is also preferably 7 to 10 days. When culturing leaf piece explants using the two short cultures, the time of the cultures should be less than 7 days since root initiation will begin within a 7 day time period. Whether one or two high auxin cultures of short time duration are used, the resultant tissue is then subcultured on shoot regeneration media.

Various auxins and cytokinins may be used in this auxin pulsing process. The amount of auxin and cytokinin for optimum morphogenic callus regeneration depends on the specific auxin and cytokinin combination and is separately determined by factorial experiments for each auxin/cytokinin combination. The auxin concentration is high in order to promote the regeneration of morphogenic calli.

IAA with BA is the preferred auxin/cytokinin combination, with the amounts of IAA and BA being respectively 10 mg/l and 0.05 mg/l in the first high auxin culture and 5 mg/l and 0.05 mg/l in the second high auxin culture. Other usable auxins are: 2,4-D, NAA, and indolebutyric acid (IBA). Other usable cytokinins are: zeatin, kinetin, and isopentenyl adenine (2iP). The ratios of NAA, IBA, and 2,4-D to BA or kinetin are 100 to 1 in the first high auxin culture and 50 to 1 in the second. The ratios of NAA, IBA, and 2,4-D to zeatin or 2iP are 50 to 1 in the first high auxin culture and 25 to 1 in the second. The ratios of IAA to zeatin or 2iP are 100 to 1 in the first high auxin culture and 50 to 1 in the second. The ratios of IAA to kinetin are 200 to 1 and 100 to 1.

In one embodiment of the auxin pulsing process, using IAA and BA, explants are cultured in darkness for 7 to 10 days on MS supplemented with a high concentration of IAA at 10 mg/l and with 0.05 mg/l BA. These explants are then immediately subcultured in darkness for a second 7 to 10 day period on MS supplemented with a second high concentration of IAA, less than the first, at 5 mg/l, and with 0.05 mg/ BA. After this IAA pulsing, the explants are then subcultured on MS with 0.1 mg/l BA in the light for continued tissue regeneration.

A second embodiment of the auxin pulsing process is identical to the first embodiment except that the first high auxin culture with the concentration of IAA at 10 mg/l is omitted. Instead, the IAA pulsing consists only of one 7 to 10 day culture in darkness at the lower IAA concentration of 5 mg/l.

The auxin pulsing technique has general applicability wherever, a high frequency of tissue regeneration in vitro is needed and is directly applicable to the development of tolerance to toxic chemicals by tree tissue in vitro. Either the one culture or two culture auxin pulsing procedures may be used in developing tolerance to toxic chemical. After the auxin pulsing, the plant tissue is further cultured on a tissue regeneration medium while contacting the tissue with the toxic chemical against which tolerance is to be developed. In a preferred embodiment, the regeneration medium is MS with 0.1 mg/l BA and the tissue is contacted with the toxic chemical by including the chemical in the regeneration medium. Preferably, the chemical is present at the concentration which is 100% lethal to tissue cultures of the normal non-tolerant plant throughout the further culturing. The plant tissue is subcultured in the presence of the toxic chemical sufficiently to insure that any surviving tissue has developed tolerance to the chemical by subculturing for a total period of time necessary to insure necrosis of any non-tolerant tissue. Preferably, the plant tissue is subcultured continuously three times with each subculture lasting thirty days. A thirty day time period for each subculture is used because this is the time in which the subculture medium becomes substantially exhausted. The time period of each subculture may be modified as warranted based on nutrient demands and toxic chemical breakdown.

After the exposure to the toxic chemical, any surviving tissue is continuously subcultured on tissue regenerating medium without toxic chemical until shoots of a predetermined size have grown. Plantlets are then developed. These post-exposure process steps are identical to those of the maximized growth regulator ratio process.

In addition to the foregoing methods, somatic embryogenesis provides a means for regenerating a large number of plants and may be used to supply somaclonal variants tolerant of toxic chemical.

Initially, explants from shoot cultures grown chemically are callused in darkness to regenerate proglobular embryogenic callus cells therefrom using a solid MS medium having 5 mg/l 2,4-D, 0.5 rag/l BA, 30 g/l sucrose, 20 micromoles glutamine and 6 g/l agar. Subculturing of the explants may be continued by transferring to fresh medium of the same type, each subculture being for a thirty day period.

The embryogenic callus cells formed are transferred to liquid medium in order to generate additional embryogenic callus cells until the number desired for further processing has been generated. A preferred liquid medium for generating a large number of additional embryogenic callus cells is MS with 1 mg/l 2,4-D, 0.05 mg/l BA and 30 g/l sucrose. The 2,4-D to BA ratio and sucrose concentration are selected to optimize subsequent embryo induction and early embryo development. The cell suspension is continuously agitated during the liquid culture. Subculturing may be continued by transferring to fresh medium at regular intervals. In the preferred embodiment, the initial liquid subculture is conducted for a period of three weeks. Samples are then taken therefrom and placed in fresh liquid medium for shorter subcultures of 1 week each in duration.

Culturing to form proglobular embroygenic callus cells is conducted with an agent preventing embryo formation. In the preferred embodiment, embryo formation is prevented by 2,4-D. When a sufficient number of cells has been generated, addition of 2,4-D is stopped. Embryogenesis then proceeds in the absence of the 2,4-D from the medium.

Alternatively, a large number of embryogenic callus cells may be generated by continuing the initial solid medium culture and, when the desired number of embryogenic callus cells has been generated, reducing or eliminating the embryo-preventing compound to permit the formation of somatic embryos in the solid medium culture. The somatic embryos differentiate directly on the stem and leaf explants.

Once application of the embryo-preventer is reduced or stopped, globular embryos form after 5 weeks whether using liquid or solid medium. In liquid media, agitation is continued during this phase. Once the embryos have grown to the torpedo-shaped stage, they are transferred to a medium which causes the somatic embryos to germinate. A preferred germination medium is MS with 5 mg/l IAA and 0.5 mg/l BA. Subculturing for an appropriate period of time on this medium, 1 week being preferred, will cause the embryos to germinate. Germinated embryos are then transferred to an appropriate soil mix for growth into whole plants.

Regeneration by somatic embryogenesis may be used in the selection of somaclonal variants having toxic chemical tolerance. Aliquots of proglobular embryogenic callus cells from the liquid or solid callus cell cultures are plated on a medium inducing embryogenic callus cell growth, preferably solid embryogenic basal agar medium comprising MS with 1 mg/l 2,4-D, 0.05 mg/l BA and 30 g/l sucrose. The medium also includes a concentration of the toxic chemical for which tolerance is to be developed present at a concentration at or below the 100% lethal level. After a time period during which the medium is consumed, e.g. 60 days, surviving cells are subcultured onto fresh cell growth medium having an increased concentration of toxic chemical. Surviving cells are continuously subcultured in this manner in successive subcultures having ever increasing concentrations of the toxic chemical. The gradual increase in toxic chemical concentration is an important element of the process. If chemical exposure is started at a high concentration level, the large mass of dying cells likely to be produced could result in the killing of neighboring tolerant cells. During this testing for chemical tolerance, the presence of an embryo-preventing chemical is maintained so that only proglobular cells are generated. Embryo formation is not allowed to occur until the toxic chemical exposure is completed. Successive subculturing is continued until a concentration of toxic chemical is reached equal to or greater than the 100% lethal level. Any cells surviving at this concentration of toxic chemical are then treated, without further toxic chemical or embryo preventer, for somatic embryo formation, germination and growth into whole plants. In a preferred embodiment, successive subculturing is continued until a concentration of toxic chemical is reached which no cell survives. During the successive subculturing, a portion of the cells surviving the increasing toxic chemical concentrations are recovered. Then, cells surviving the immediately preceding subculture are further processed, these being the cells which survive the highest survivable concentration of toxic chemical. These survivor cells are then treated, without the further application of toxic chemical or embryo preventer, to achieve somatic embryo formation, germination and growth into whole plants.

The plant tissues produced by these processes, and the plantlets and trees grown therefrom, are tolerant of chemicals normally toxic to the parent genotype in that the plant tissues, plantlets and resulting trees survive an application of the toxic chemical at a concentration equal to or greater than the concentration 100% lethal to the tree's parent genotype at the corresponding level of growth development. For example, with reference to Table 8, plants of the four hybrid Populus clones listed are tolerant of the herbicides glyphosate or sulfometuron methyl at the listed concentrations which are higher than the highest concentrations lethal to each tree's normal, non-tolerant parent genotype. Since the tolerant plants are produced by processes which utilize somaclonal variation arising during in vitro culturing, the plants produced have a genome derived only from that of the parent clone. No foreign genes are introduced from an outside source.

The following examples are only illustrative of the embodiments of the invention. Changes and modifications in these specific examples, as in the foregoing embodiments, can be carried out without departing from the scope of the invention which is intended to be limited only by the scope of the claims.

EXAMPLE 1

Continuous shoot regenerating cultures of Populus hybrids were first established to provide stock plant material for the development of herbicide tolerant Populus trees and for the present rapid high-frequency plant tissue regeneration techniques. The Populus hybrids used were NC-5339, NC-5272, NC-11390, NC-5331 and NC-5326. These are further described in Table 1.

Shoot tips of 2 cm in length were cut from hedged greenhouse stock plants of the Populus hybrids, placed in sterile water with commercial dishwashing detergent, sterilized in a 10% bleach solution for 10 minutes, and rinsed 3 times in sterile purified water. The shoot tips were placed horizontally in GA-7 culture vessels on 50 ml of basal Murashige and Skoog (MS) medium (1962) containing 100 mg/l myoinositol, 200 mg/l casein hydrolysate, 20 g/l sucrose, and 0.1 mg/l benzyladenine (BA), solidified with 0.6% Difco Bacto agar (pH 5.8). The shoot cultures were then kept in a growth room at 26° C. in cool white light (30 microeinsteins $m^{-2} sec^{-1}$) with an 18 hour photoperiod. Shoot production occurred from both adventitious origin and axillary buds. These shoot regenerating cultures were subcultured every 3–4 weeks on the identical medium. Subculturing involved either transfer of the entire shoot mass to fresh basal medium or placing a 2–3 cm shoot tip vertically (NC-5331, NC-11390, NC-5272 and NC-5326) or horizontally (NC-5339) into the medium. In the case of NC-5339, the apical shoot tips were first removed.

These continuous shoot cultures supplied the beginning plant tissue material for the following examples.

EXAMPLE 2

Determinations were made of the maximized growth regulator ratios for producing the greatest frequency of Populus tissue regeneration from nodal stem pieces, leaf pieces or leaf disks of the hybrid Populus plant stock material of Example 1 using growth regulators NAA and BA. Adventitious shoot and root regeneration was achieved for the five Populus hybrids of Example 1.

Nodal stem pieces (1 cm in length), leaf pieces with their apical and basal ends removed, or leaf disks punched out with a #5 cork borer, were obtained from the stock plant material of the five hybrid Populus clones of Example 1. Factorial experiments were then conducted with varying amounts of the plant growth regulators BA and NAA. A 5×5 factorial arrangement of the growth regulators was used with concentrations of each at 0, 0.01, 0.1, 1.0 and 5.0 mg/l. The remainder of the growth medium comprised MS media supplemented with 100 mg/l myoinositol, 200 mg/l casein hydrolysate, and 20 g/l sucrose, solidified with 0.6% Difco Bacto agar (pH 5.8).

The nodal stem pieces, leaf pieces or leaf disks were placed one per quadrant in disposable quad petri plates which were then wrapped with parafilm. Two replications with four samples each were placed in a randomized complete block design that was repeated twice. All samples were placed in the same environmental conditions as were used for the stock cultures of Example 1.

After six weeks, the cultures were scored for root and shoot production and for callus quality. The highest rating for callus quality was given for the greatest amount of friable, organogenic callus produced. Table 2 lists those combinations of growth regulators which resulted in the most shoot, root or morphogenic callus regeneration, from nodal stem exploits and from leaf explants of each poplar hybrid. The mean values of the root and shoot regeneration are presented together with the standard error.

Regarding shoot regeneration using leaf pieces, the maximized growth regulator ratio was different for 4 out of the 5 clones and the number of adventitious shoots regenerated varied depending on the clone usual, although the highest cytokinin/auxin ratio resulted in the greatest number of adventitious shoots. Shoot formation was greatest across clones at a BA:NAA ratio of at least 1:1, and in most cases at a higher ratio.

Root regeneration using leaf pieces was greater than shoot regeneration from leaf pieces in all clones. Root formation was maximized in most cases at greater than a 10:1 ratio of NAA:BA. Except for NC-5339, which produced few roots regardless of explant type, all clones produced the most. roots from leaf explants. Adventitious rooting was greatest from leaf segments of NC-5331 when comparing explant source and all clones.

Treatments producing the best morphogenic callus had NAA:BA ratios exceeding 10:1. Callus quality from node explants of NC-5331 was the best of all clones and resulted from the highest auxin-to-cytokinin ratios. NC-5326 and NC-5339 were the least responsive to NAA:BA treatments with the same explants.

Leaf segments of NC-5331 and NC-11390 produced the most roots and callus after NAA:BA treatments.

NC-11390 produced shoots from nodal segments from a wider range of treatments than all other clones.

TABLE 2

Treatments that generated the maximum number of roots and shoots and the most meristematic callus utilizing factorial combinations of benzyladenine (BA) and naphthaleneacetic acid (NAA).

| CLONE | EXPLANT | SHOOT NUMBER | | | ROOT NUMBER | | | CALLUS | |
|---|---|---|---|---|---|---|---|---|---|
| | | TREATMENT (mg/l) | | MEAN | TREATMENT (mg/l) | | | TREATMENT (mg/l) | |
| | | BA | NAA | (±SE) | BA | NAA | MEAN (±SE) | BA | NAA |
| NC-5339 | node | 1.0 | 1.0 | 16.3 ± 2.3 | 0 | 0.1 | 2.1 ± 0.1 | 0.1 | 5.0 |
| | leaf | 1.0 | 1.0 | 16.1 ± 1.1 | 0 | 5.0 | 0.4 ± 0.1 | 1.0 | 5.0 |
| NC-5331 | node | 1.0 | 0.1 | 31.3 ± 6.3 | 0 | 1.0 | 2.8 ± 0.4 | 0.1 | 1.0 |
| | leaf | 1.0 | 1.0 | 2.5 ± 0.4 | 0.1 | 5.0 | 58.8 ± 12.6 | .01 | 5.0 |

TABLE 2-continued

Treatments that generated the maximum number of roots and shoots and the most meristematic callus utilizing factorial combinations of benzyladenine (BA) and naphthaleneacetic acid (NAA).

| CLONE | EXPLANT | SHOOT NUMBER TREATMENT (mg/l) BA | NAA | MEAN (±SE) | ROOT NUMBER TREATMENT (mg/l) BA | NAA | MEAN (±SE) | CALLUS TREATMENT (mg/l) BA | NAA |
|---|---|---|---|---|---|---|---|---|---|
| NC-11390 | node | 1.0 | 0.01 | 33.0 ± 8.1 | 0.1 | 1.0 | 5.5 ± 0.7 | .01 | 5.0 |
|  | leaf | 1.0 | 0.1 | 29.5 ± 3.4 | 0 | 1.0 | 41.2 ± 6.9 | .01 | 1.0 |
| NC-5272 | node | 0.1 | 0.01 | 16.8 ± 1.3 | 0 | 0.1 | 4.3 ± 1.6 | .01 | 5.0 |
|  | leaf | 0.1 | 0.1 | 3.5 ± 0.6 | .01 | 1.0 | 9.5 ± 1.2 | .01 | 5.0 |
| NC-5326 | node | 0.01 | 0.01 | 2.3 ± 0.1 | 0 | 0.1 | 0.7 ± 0.1 | .01 | 5.0 |
|  | leaf | 0 | 1.0 | 1.2 ± 0.3 | .01 | 1.0 | 17.5 ± 3.2 | 0 | 5.0 |

EXAMPLE 3

Populus plant stock material was then cultured on the maximized shoot regeneration media of Example 2 in the presence of a herbicide for which tolerance was to be developed.

Leaf pieces (NC-5331, NC-11390, and NC-5272) and leaf disks (NC-5339) were grown directly on each hybrid's maximized culture medium as determined in Example 2, each medium however also containing either the herbicide glyphosate or the herbicide sulfometuron methyl, exposure to the herbicide occurring before the tissue had begun to initiate adventitious shoots. The concentrations of glyphosate and sulfometuron methyl used are set forth in Table 3.

TABLE 3

Concentrations of glyphosate and sulfometuron methyl used in selection medium for regeneration of somaclonal variants with herbicide tolerance

| Herbicide | Concentrations |
|---|---|
| Glyphosate | 0, 100, 250, 500, 1000 micromoles/l |
| Sulfometuron methyl | 0, 10, 25, 50, 75, 100 ppb |

The leaf pieces or disks were kept on the herbicide-amended media in the dark for an initial 30-day subculture. After this initial exposure, the surviving leaf pieces or disks were transferred to the same shoot regeneration media but with 0.1 mg/l BA as the only growth regulator and with herbicide now absent. Leaf pieces or disks were continually subcultured at 30-day intervals in this same media in the light until shoots greater than 1 cm had been regenerated.

EXAMPLE 4

Prior to rechallenging the shoots of Example 3 with herbicide to determine those possessing herbicide tolerance, a determination was made of the level of glyphosate and of sulfometuronmethyl lethal to unselected shoot tips of the five Populus clones being tested. The lethal dosage levels ($LD_{100}$) thus determined were then used to screen putative tolerant regenerants of all clones from Example 3 to eliminate any non-tolerant shoots.

Shoot tips (2 cm) from the continuous shoot cultures of Example 1 were vertically explanted into petri plates with MS+0.1 mg/BA+20 g/l sucrose and solidified with 0.6% Difco Bacto agar. Glyphosate was added (filter-sterilized) before solidification at final concentrations of 0, 5, 10, 25, 50, 75, 100, 250, 500 and 1000 micromoles/l. Sulfometuron methyl was added at the following final concentrations: 0, 1, 2.5, 5, 7.5, 10, 25, 50, 75 and 100 ppb. The shoot cultures were grown in the light for 4 weeks and analyzed for necrosis.

The $LD_{100}$ concentrations, i.e. the natural maximum tolerance levels, for the shoot tips of each of the 5 clones with respect to each herbicide are listed in Table 4.

TABLE 4

Herbicide concentrations ($LD_{100}$)[a] used to rechallenge putative somaclonal variants with herbicide tolerance

| Populus hybrid clones | Glyphosate (micromoles/l) | Sulfometuron methyl (ppb) |
|---|---|---|
| NC-5339 | 50 | 50.0 |
| NC-5331 | 250 | 2.5 |
| NC-5272 | 75 | 1.0 |
| NC-11390 | 75 | 5.0 |

[a]$LD_{100}$ = Dosage of herbicide in agar medium that is 100% lethal for vertically explanted Populus shoot tips

EXAMPLE 5

Those regenerated shoots of Example 3 greater than 1 cm were then rechallenged for 3 consecutive 30-day periods on MS medium containing 0.1 mg/l BA with a concentration ($LD_{100}$) of herbicide toxic to non-selected plants as determined in Example 4. Survivors were subcultured on MS medium with 0.1 mg/l BA for 3 consecutive 30-day periods.

The results of this rechallenge with herbicide are set forth in Table 5. The values in Table 5 represent the total number of plants to survive that were cultured at a lethal dose or higher and then rechallenged at a lethal dose; i.e. the total number of all shoots grown at concentrations greater than $LD_{100}$.

TABLE 5

Frequency of regeneration of herbicide tolerant shoots[a] following rechallenge with toxic concentrations of glyphosate and sulfometuron methyl

| Hybrid Clone | Number and Freq. of Herbicide Tolerant Shoots Regenerated | | | |
|---|---|---|---|---|
|  | Glyphosate | | Sulfometuron Methyl | |
|  | No. | Frequency (%) | No. | Frequency (%) |
| NC-5339 | 62/2581[b] | 2.4 | 3/2322 | 0.13 |
| NC-5331 | 17/400 | 4.3 | 2/360 | 0.56 |
| NC-5272 | 26/620 | 4.2 | 36/504 | 7.10 |
| NC-11390 | 36/4720 | 0.7 | 4/4248 | 0.09 |

[a]Refer to Table 4 to determine herbicide concentrations used to rechallenge cultures for selection of tolerant somaclonal variants.
[b]Total number of tolerant shoots regenerated from leaf explants as a ratio to the possible number of shoots that could have been regenerated in the absence of herbicide.

Following rechallenge with glyphosate, the greatest number of tolerant microplants remained in the hybrid clone NC-5339 and the fewest NC-5331. Despite the lower numbers of tolerant microplants in NC-5272 and NC-5331, they were the most efficient producers of tolerant shoots, 4.2% and 4.3%, respectively.

Following rechallenge with sulfometuron methyl, NC-5272 had the greatest number of remaining tolerant shoots (36) and was the most efficient producer at 7.1%. The other 3 clones produced only a few shoots, with NC-11390 being the least efficient with 4 shoots remaining out of 4248 possible regenerants.

Subsequently, the shoots surviving the rechallenge were rooted to produce plants for greenhouse testing.

EXAMPLE 6

Leaf pieces of NC-11390 were initially subcultured in darkness for 30 days on the appropriate maximized shoot regeneration media of Example 2 in the presence of sulfometuron methyl. The medium was MS medium supplemented with 1 mg/l BA, 0.1 mg/l NAA and 20 g/l sucrose and treated with sulfometuron methyl at concentrations of 0, 10, 25, 50, 75 and 100 ppb, these all being concentrations of sulfometuron methyl greater than the LD100 concentration of 5 ppb. Four samples with six replications each were used at each sulfometuron methyl concentration.

Leaf pieces surviving this initial herbicide exposure were immediately subcultured on MS medium with 0.1 mg/l BA and the original concentrations of the sulfometuron methyl for 3 consecutive 30-day periods in the light. Shoots that survived this treatment at these concentrations greater than the $LD_{100}$ concentration were subcultured for 3 consecutive 30-day periods on MS+0.1 mg/l BA medium. The numbers of shoots surviving this procedure for each level of sulfometuron methyl are listed in Table 6.

TABLE 6

Number of putative sulfometuron methyl tolerant shoots regenerated in vitro after selection on herbicide-containing medium for four thirty-day periods

| Sulfometuron Methyl (ppb) | Adventitious Shoots Number | % of Control |
|---|---|---|
| 0 | 708 ± 76 | — |
| 10 | 5 | .7 |
| 25 | 1 | .1 |
| 50 | 0 | 0 |
| 75 | 0 | 0 |
| 100 | 0 | 0 |

From a possible regeneration of 708 shoots in this experiment, 6 putative tolerant microshoots resulted. Five were from the 10 ppb treatment and 1 from the 25 ppb treatment. Thus, increased tolerance to sulfometuron methyl was achieved at levels 2 to 5 fold over the dose lethal to normally non-tolerant microshoots, i.e. 10 and 25 ppb versus 5 ppb. Following the selection on the herbicide-containing media and after reculturing on shoot regeneration medium, normal phenotypical characteristics and in vitro growth rate resumed.

Those surviving shoots equal to or greater than 2 cm in length were then rooted ex vitro in Ekco foil trays in non-sterile soil-less mix and transferred to the greenhouse for later testing for tolerance to sulfometuron methyl spray. If the tolerant microshoots were equal to or greater than 2 cm in length, their rooting in non-sterile soil-less rooting mix was 100% successful. These rooted shoots were then successfully transferred to the greenhouse with no loss of plant material.

EXAMPLE 7

A medium comprising BA and zeatin was tested as an alternative maximized growth medium for producing high frequency Populus tissue regeneration for the challenging of Populus plant material. The medium gave a high frequency of Populus tissue regeneration although not as high as the media of Example 2.

Leaf disks of NC-5339 (made with a #5 cork borer) from leaves of the continuous shoot cultures of Example 1 were explanted on MS medium supplemented with 1 mg/l BA, 1 mg/l zeatin and 20 g/l sucrose. The leaf disks were simultaneously treated with glyphosate at concentrations of 0, 100, 250, 500 and 1000 micromoles (active ingredient as ROUNDUP. Treatment of the leaf disks with glyphosate was either by including the glyphosate in the medium or by pre-dipping the leaf disks in glyphosate before explanting. Four samples with 8 replications each were use<]for each glyphosate treatment.

The leaf disks were grown on the media for an initial 30 day subculture in the dark. Surviving leaf disks were then transferred to herbicide-free shoot regeneration medium, i.e. MS with 0.1 mg/l BA as the only growth regulator. The leaf disks were then continuously subcultured for four 30-day intervals on this medium free of herbicide in the light during which shoots differentiated from green areas of the leaf disks.

Using the $LD_{100}$ concentration for NC-5339 of 100 micromoles per liter from Table 4, the putative tolerant shoots regenerated were then rechallenged for 3 consecutive 30-day subcultures on MS with 0.1 mg/l BA and with the $LD_{100}$ concentration of herbicide toxic to normal plants.

Shoots which survived the rechallenge on the glyphosate-amended medium for three consecutive subcultures were rooted ex vitro in non-sterile soil-less rooting mix and transferred to the greenhouse for later spray testing. The results are tabulated in Table 7, which lists the number of glyphosate tolerant shoots regenerated in vitro after initial selection and following three rechallenges with glyphosate used as a pre-dip or added to the medium. Shoots were regenerated either when the original leaf explant was dipped in glyphosate or when the leaf disk was explanted directly onto glyphosate-amended medium.

TABLE 7

Number of putative glyphosate tolerant shoots regenerated in vitro after initial selection and following three rechallenges with glyphosate used as a pre-dip or added to the medium

| Glyphosate (micromoles) | Shoots (initial selection) | | Shoots (rechallenge) | |
|---|---|---|---|---|
|  | Leaf Dip | Media | Leaf Dip | Media |
| Control | 516 ± 78 | 537 ± 67 | 516 ± 78 | 537 ± 67 |
| 100 | 3 | 9 | 1 | 0 |
| 250 | 10 | 29 | 2 | 2 |
| 500 | 24 | 6 | 2 | 4 |
| 1000 | 29 | 3 | 5 | 3 |

More putative tolerant shoots were regenerated from glyphosate dip treatments, but following rechallenge with herbicide, the number of shoots surviving was not significantly different between the two techniques. Most of the shoots regenerated at 500 and 1000 micromoles glyphosate using the leaf dip method were killed with three rechallenges at the $LD_{100}$ concentration of glyphosate. With the leaf dip method, therefore, there was a greater chance of regenerating non-tolerant shoots that did not survive herbicide rechallenge.

Abnormal leaf morphology was apparent with either herbicide dipping or herbicide-amended medium. Instead of broad, ovate leaves, thin strap-like leaves are produced temporarily at the first rechallenge. Glyphosate was therefore able to affect gene regulation of the shoot morphology of in vitro tolerant shoots. Upon removal of glyphosate from the medium, normal leaf morphology returned with differentiation of new leaves from the growing shoot tips. Following the rechallenges, tolerant shoots greater than 2 cm in length rooted 100% successfully in non-sterile soil-less rooting mix. They were then successfully transferred to the greenhouse with no loss of plant material.

EXAMPLE 8

Node-containing stem segments 1 cm in length and leaf pieces comprising leaves with their apical and basal ends removed of NC-5339, NC-5272, NC-11390 and NC-5331 were grown on MS medium supplemented with IAA and BA.

Two growth methods were used. In the first method a high concentration of IAA at 10 mg/l and 0.05 mg/l BA in MS were used as the medium. Explants were placed on the medium in 100×15 mm disposable petri dishes and kept in darkness for 7–10 days. Then the explants were subcultured onto plates containing MS plus 5 mg/l IAA and 0.05 mg/l BA for an additional 7–10 days in darkness. The explants were then subcultured onto petri plates containing MS plus 0.1 mg/l BA and placed in the light. After 30 days in the light, cultures were evaluated for root and shoot production.

The second method was identical to the first except there was no initial culture on MS with 10 mg/l IAA and 0.05 mg/l BA. Otherwise this method was identical to that for the first method.

Figure 1B:
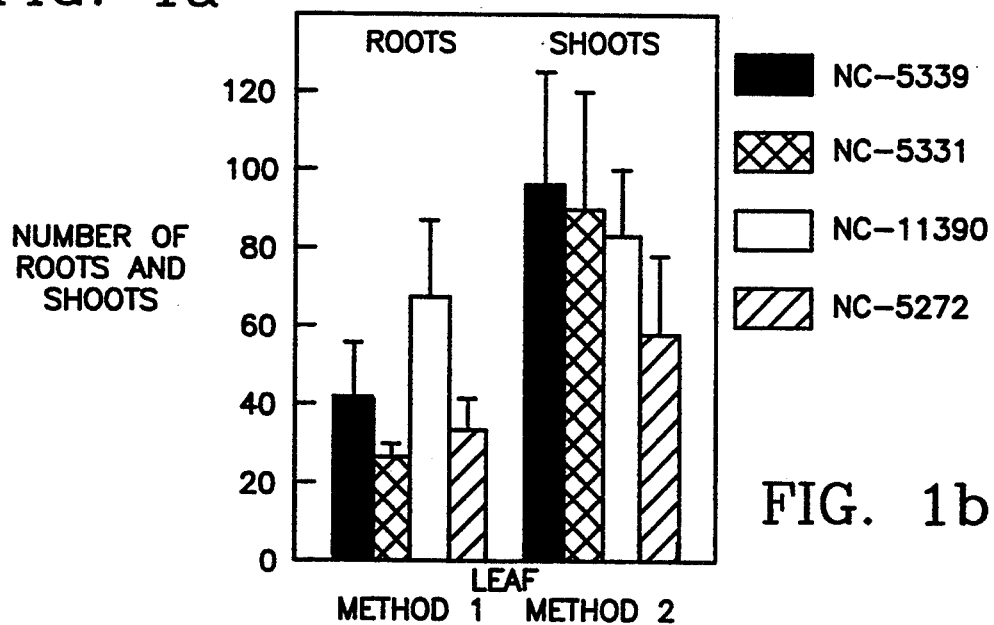
FIGS. 1b and 1c show in graph form the output from the auxin pulsing embodiments in Example 8.
Figure 1C:
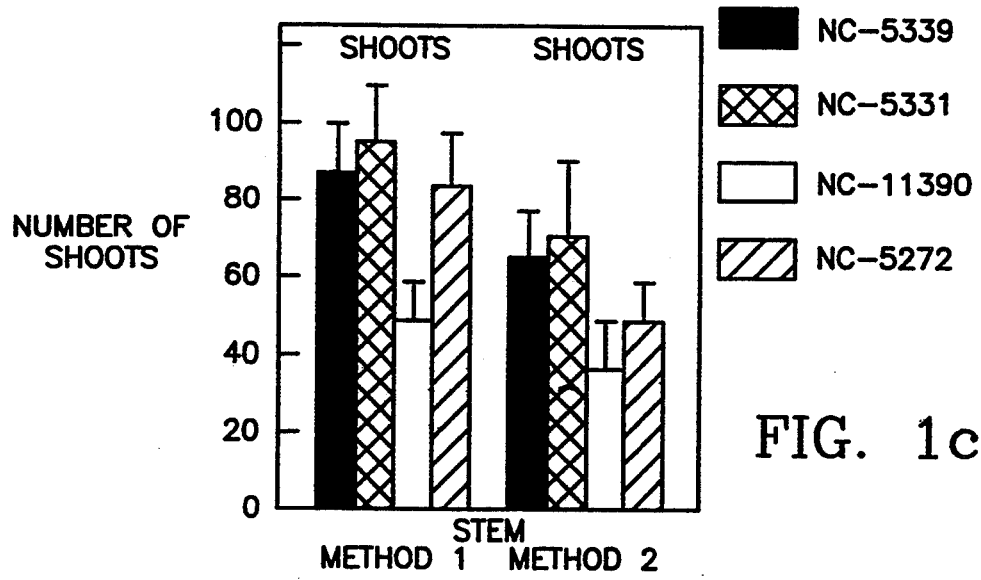

The results are set forth in graph form in FIG. 1.

More shoots were regenerated using the IAA pulsing of these two methods than using MS medium maximized with NAA and BA as set forth in Example 2. Shoot regeneration under the first pulsing method using node explants of all the clones except NC-11390 resulted in at least three times the number of shoots produced with a maximized NAA and BA supplemented medium. The second pulsing method produced similar results for regenerating shoots from leaf explants.

EXAMPLE 9

Stock plants grown from shoots produced by the processes of Examples 5, 6 and 7 were tested for their tolerance to glyphosate or sulfometuron methyl.

Nine centimeter lateral shoot cuttings were removed from the stock plants and from plants of the non-selected parent clones. The end of each cutting was dipped in rooting compound, e.g. 1000 ppm nitrophenyl-IBA, and was then placed vertically in a 4" plastic pot containing commercial potting mix (Rediearth). The heights of the cuttings in the pots were adjusted so that each was the same height above the top edge of its pot. The cuttings were rooted under mist propagation for three weeks and then grown for one additional week on a greenhouse bench. The resulting plants were sprayed with dust, a commercial formulation of sulfometuron methyl, at 0, 50, 100, 500, 1000 or 2000 ppm (the equivalent sulfometuron methyl concentrations respectively being 0, 0.137, 0.274, 1.37, 2.74 and 5.48 mmol/l), or with Roundup, a commercial formulation of glyphosate, at 0, ¼, ½ and ¾ lb/acre (the equivalent glyphosate concentrations respectively being 0, 5.25, 10.50 and 15.75 mmole/l). Spraying was conducted using the apparatus and procedure described in "Microspray Applicator and Enclosure for Administering Chemicals to Plants", by Bauer and Michler, *HortScience* 24 (4):704 (August, 1989). The plants were measured weekly for four weeks. After four weeks, the death of terminal shoot tips and differences in growth rate indicated those plants which were tolerant of the herbicide applications.

The results, listed in Table 8, show an increase in sulfometuron methyl tolerance to a level more than twice the dose normally lethal to rooted softwood cuttings of tissue culture regenerated control plants. Biochemical assays of crude extracts from the tolerant plants indicated that the enzyme which sulfometuron methyl targets, acetohydroxyacid synthase, had greater total activity and less sensitivity to sulfometuron methyl compared with control plants.

TABLE 8

| | Normally lethal herbicide dosages and dosages which tolerant plants survive | | | |
|---|---|---|---|---|
| | Glyphosate (mmole/l) | | Sulfometuron methyl (mmole/l) | |
| Clone | Normally Lethal Level | New Level of Tolerance | Normally Lethal Level | New Level of Tolerance |
| NC-5272 | 10.50–15.75 | >15.75 | .882 | 1.37 |
| NC-5331 | 10.50–15.75 | >15.75 | .685 | — |
| NC-11390 | 10.50–15.75 | >15.75 | .685 | >1.37 |
| NC-5339 | 10.50 | >13.12 | .685 | — |

The mmole/l concentration is that of the active ingredient as isopropylamine salt of glyphosate in ROUNDUP or as sulfometuron methyl in OUST.

EXAMPLE 10

Somatic embryogenesis was used to regenerate plants. Stem and leaf explants from sterile stock cultures of the hybrid *Populus alba* L.×*Populus grandidentata* Michx. (NC-5339) were treated to form proglobular callus clumps by culturing them in darkness on MS medium with 5 mg/l 2,4-D, 0.5 mg/l BA, 30 g/l sucrose, 20 micromoles glutamine and 6 g/l agar. Culturing on solid medium was continued by further subculturing on identical solid medium. When leaf pieces were thus cultured, embryogenic callus cells generally formed along the leaf veins.

Additional enbryogenic callus cells were generated by transferring from the solid medium 1 gram of the cells formed to liquid medium comprising MS with 1 mg/l 2,4-D, 0.05 mg/l BA and 30 g/l sucrose while continuously agitating the liquid suspension on a gyratory shaker at 150 rpm. After an initial subculture for three weeks, 5 ml samples of the cell suspension were each transferred to 50 ml of fresh medium. The cultures were maintained further by subculturing every 7 days with continuous agitation.

Embryogenesis proceeded in the liquid culture upon ceasing the addition of 2,4-D and in the solid culture upon reducing the 2,4-D addition to 1.0 mg/l. In the liquid culture, somatic embryos formed after two 7-day subcultures. Globular embryos formed after 5 weeks whether using liquid or solid medium. Once torpedo-shaped somatic embryos formed, they were germinated in MS medium supplemented with 5 mg/l IAA and 0.5 mg/l BA.

EXAMPLE 11

Using somatic embryogenesis to develop genetically variant hybrid Populus clones with increased tolerance to glyphosate or sulfometuron methyl, cell suspension cultures were initiated with callus derived from leaf and internode pieces of continuous shoot cultures of the five Populus clones listed in Table 1. Aliquots from these embryogenic cell suspension cultures were plated on solidified MS medium containing 1 mg/l 2,4-D, 0.05 mg/l BA, 30 g/l sucrose, and either glyphosate or sulfometuron methyl. Surviving cells were subcultured every 60 days onto the same medium but with increased herbicide concentration. Glyphosate was supplied initially at 250 micromoles/l, then incrementally increased to 500, 1000, 1500, and 2000 micromoles/l at each successive subculture. Sulfometuron methyl was added initially at 14 nmol/l and increased to 27, 54, 108, and 216 nmol/l.

TABLE 9

| | Normally lethal herbicide dosages and dosages which tolerant embrogenic callus cells survive | | | |
|---|---|---|---|---|
| | Glyphosate (micromole/l) | | Sulfometuron methyl (nmole/l) | |
| Clone | Normally Lethal Level | New Level of Tolerance | Normally Lethal Level | New Level of Tolerance |
| NC-5272 | $\leq 500$ | 1000 | $\leq 14$ | 54 |
| NC-5331 | $\leq 500$ | 1000 | $\leq 14$ | 54 |
| NC-11390 | $\leq 500$ | — | $\leq 14$ | 27 |
| NC-5326 | $\leq 500$ | — | $\leq 14$ | 27 |
| NC-5339 | $\leq 500$ | — | $\leq 14$ | — |

The concentrations are that of the active ingredient as isopropylamine salt of glyphosate in ROUNDUP or as sulfometuron methyl in OUST.

Embryogenic calli were isolated that tolerated glyphosate and sulfometuron methyl at each toxic level for all five Populus clones tested. For three of the five clones tested, the calli having new, higher tolerance levels were successfully developed into germinated somatic embryos which regenerated plants acclimated ex vitro. Table 9 lists the tolerance levels of the normal parent genotypes of the five clones tested and the new tolerance levels for those clones whose embryogenic calli produced plants successfully acclimated ex vitro.

We claim:

1. A Populus hybrid plant capable of surviving an application of a toxic chemical selected from the group consisting of sulfometuron methyl and glyphosate at a concentration equal to or greater than the concentration that is 100% lethal to the plant's parent hybrid genotype;

the plant being a hybrid Populus clone selected from the group consisting of: P. alba×P. grandidentata capable of surviving glyphosate applied at at least 10.50 mmole/l up to and including 13.12 mmole/l; P. nigra×P. laurifolia capable of surviving glyphosate applied at about 15.75 mmole/l; P. maximowiczii×P. trichocarpa capable of surviving glyphosate applied at about 15.75 mmole/l; P. nigra betulifolia×P. trichocarpa capable of surviving glyphosate applied at about 15.75 mmole/l; P. nigra×P. laurifolia capable of surviving sulfometuron methyl applied at at least 0.882 mmole/l up to and including 1.37 mmole/l; and, P. maximowiczii×P. trichocarpa capable of surviving sulfometuron methyl applied at at least 0.685 mmole/l up to and including 1.37 mmole/l; and, the plant having a genome derived only from the genome of the Populus parent hybrid, the plant being a somaclonal variant of the parent hybrid genotype with its survival capability arising from the somaclonal variation.

2. A method for regenerating Populus shoots tolerant of a toxic chemical at a concentration normally lethal thereto, comprising:

culturing tissue of a Populus genotype selected from the group consisting of: P. alba×P. grandidentata; P. nigra×P. laurifolia; P. maximowiczii×P. trichocarpa; and, P. nigra betulifolia×P. trichocarpa, with a tissue regeneration medium having indoleacetic acid at a concentration of 5 mg/l and benzyladenine at a concentration of 0.05 mg/l, the culturing being conducted for a period of time up to ten days, for regenerating a high number of morphogenic callus cells of the Populus genotype; and, subsequently subculturing the morphogenic callus cells with a shoot regeneration medium while contacting the morphogenic callus cells during the subsequent subculturing with a chemical toxic to the Populus genotype for a period of time sufficient to insure that any surviving shoot has tolerance to the chemical at the normally lethal concentration, the toxic chemical being selected from the group consisting of glyphosate and sulfometuron methyl.

3. The method of claim 2, and including:

prior to the tissue culturing, preliminarily culturing tissue of the Populus genotype with a tissue regeneration medium having indoleacetic acid at a concentration higher than 5 mg/l and benzyladenine at a concentration of 0.05 mg/l, the preliminary culturing being conducted for a period of time up to ten days, for regenerating a high number of morphogenic callus cells, the tissue cultured with the 5 mg/l indoleacetic acid medium being morphogenic callus cells from the preliminary culture.

4. The method of claim 3, wherein:

the indoleacetic acid concentration of the preliminary culture is 10 mg/l.

5. The method of claim 3, wherein the tissue culturing and the preliminary culturing are each conducted in darkness.

6. The method of claim 2, wherein the shoot regeneration medium comprises benzyladenine at a concentration of 0.1 mg/l.

7. A method for the high frequency regeneration of Populus shoots, comprising:

culturing tissue of a Populus genotype selected from the group consisting of: P. alba×P. grandidentata; P. nigra×P. laurifolia; P. maximowiczii×P. trichocarpa; and, P. nigra betulifolia×P. trichocarpa, with a tissue regeneration medium having indoleacetic acid at a concentration of 5 mg/l and benzyladenine at a concentration of 0.05 mg/l, the culturing being conducted for a period of time up to ten days, for regenerating a high number of morphogenic callus cells of the Populus genotype; and, subsequently subculturing the morphogenic callus cells with a shoot regeneration medium for regenerating a high number of Populus shoots.

8. The method of claim 7, and including:
prior to the tissue culturing, preliminarily culturing tissue of the Populus genotype with a tissue regeneration medium having indoleacetic acid at a concentration higher than 5 mg/l and benzyladenine at a concentration of 0.05 mg/l, the preliminary culturing being conducted for a period of time up to ten days, for regenerating a high number of morphogenic callus cells, the tissue cultured with the 5 mg/l indoleacetic acid medium being morphogenic callus cells from the preliminary culture.

9. The method of claim 8, wherein:
the indoleacetic acid concentration of the preliminary culture is 10 mg/l.

10. The method of claim 5, wherein the tissue culturing and the preliminary culturing are each conducted in darkness.

11. The method of claim 7, wherein the shoot regeneration medium comprises benzyladenine at a concentration of 0.1 mg/l.

12. A method for producing Populus somatic embryos tolerant of a toxic chemical at a concentration normally lethal thereto, comprising:
forming embryogenic callus cells of a Populus genotype selected from the group consisting of: P. alba×P. grandidentata; P. nigra×P. laurifolia; P. maximowiczii×P. trichocarpa; P. nigra betulifolia×P. trichocarpa; and, P. deltoides×P. nigra, by culturing tissue of the Populus genotype with a medium comprising 2,4-dichlorophenoxyacetic acid, benzyladenine, sucrose and glutamine and by subculturing embryogenic callus cells in agitated liquid medium comprising 2,4-dichlorophenoxyacetic acid, benzyladenine and sucrose;
subculturing thus formed embryogenic callus cells with embryogenic callus cell inducing medium that includes a chemical toxic to the genotype, the toxic chemical being selected from the group consisting of glyphosate and sulfometuron methyl, including subculturing the embryogenic callus cells with the toxic chemical at a concentration equal to or greater than the $LD_{100}$ concentration; and,
forming somatic embryos from any surviving embryogenic callus cells.

13. The method of claim 12, wherein the subculturing with embryogenic callus inducing medium having toxic chemical includes:
subculturing the embryogenic callus cells with embryogenic callus inducing medium that includes a chemical toxic to the genotype present at a concentration less than or equal to the $LD_{100}$ concentration; and,
further subculturing surviving embryogenic callus cells with successive callus inducing media having increasing concentrations of the toxic chemical, the further subculturing continuing to a toxic chemical concentration equal to or greater than $LD_{100}$.

14. The method of claim 12, wherein the forming of somatic embryos comprises subculturing surviving embryogenic callus cells with medium comprising benzyladenine and sucrose.

15. The method of claim 12, and including germinating the somatic embryos formed by subculturing the embryos with a medium comprising indoleacetic acid and benzyladenine.

16. The method of claim 12,
wherein the forming of somatic embryos comprises subculturing surviving embryogenic callus cells with medium comprising benzyladenine and sucrose; and,
including germinating the somatic embryos formed by subculturing the embryos with a medium comprising indoleacetic acid and benzyladenine.

17. The method of claim 12, wherein:
the embryogenic callus cell inducing medium includes chemical means for preventing embryogenic callus cells from forming somatic embryos; and,
the forming of somatic embryos from the embryogenic callus cells surviving the toxic chemical comprises subculturing the surviving cells with medium omitting the chemical preventer means.

18. The method of claim 12, wherein the medium for forming embryogenic callus cells comprises 5 mg/l 2,4-dichlorophenoxyacetic acid, 0.5 mg/l benzyladenine, 30 g/l sucrose and 20 micromoles glutamine.

19. A method for producing Populus somatic embryos, comprising:
forming embryogenic callus cells of a Populus genotype selected from the group consisting of: P. alba×P. grandidentata; P. nigra×P. laurifolia; P. maximowiczii×P. trichocarpa; P. nigra betulifolia×P. trichocarpa; and, P. deltoides×P. nigra, by culturing tissue of the Populus genotype with a medium comprising 5 mg/l 2,4-dichlorophenoxyacetic acid, 0.5 mg/l benzyladenine, 30 g/l sucrose and 20 micromoles glutamine and by subculturing embryogenic callus cells in agitated liquid medium comprising 1 mg/l 2,4-dichlorophenoxyacetic acid, 0.05 mg/l benzyladenine and 30 g/l sucrose; and,
forming somatic embryos by subculturing resulting embryogenic callus cells with a medium comprising benzyladenine and sucrose.

20. The method of claim 19, and including germinating the somatic embryos formed by subculturing the embryos with a medium comprising indoleacetic acid and benzyladenine.

21. The Populus plant of claim 1, wherein the somaclonal variation is produced and the plant is selected by a method, comprising:
culturing tissue of the plant's parent hybrid genotype with a medium inducing a high frequency of tissue regeneration, and culturing regenerated tissue with a tissue regenerating medium while contacting the tissue with the toxic chemical selected from the group consisting of sulfometuron methyl and glyphosate.

22. The Populus plant of claim 1, wherein the somaclonal variation is produced and the plant is selected by a method, comprising:
culturing tissue of the plant's parent hybrid genotype with a tissue regeneration medium including plant growth regulating hormones present in amounts inducing a high frequency of tissue regeneration, while contacting the tissue with a toxic chemical from the group consisting of sulfometuron methyl and glyphosate; and, subsequently subculturing surviving tissue with tissue regeneration medium while contacting the tissue with the toxic chemical in a concentration at least as high as the concentration lethal to the parent genotype, the subsequent subculturing being conducted for a sufficient period of time to insure that any surviving tissue has tolerance to the chemical at the normally lethal concentration.

23. A Populus hybrid plant capable of surviving an application of a toxic chemical selected from the group consisting of sulfometuron methyl and glyphosate at a concentration equal to or greater than the concentration that is 100% lethal to the plant's parent hybrid genotype;

the plant being a hybrid Populus clone selected from the group consisting of: *P. alba* × *P. grandidentata* capable of surviving glyphosate applied at from 10.50 mmole/l up to and including 13.12 mmole/l; *P. nigra* × *P. laurifolia* capable of surviving sulfometuron methyl applied at from 0.882 mmole/l up to and including 1.37 mmole/l; and, *P. maximowiczii* × *P. trichocarpa* capable of surviving sulfometuron methyl applied at from 0.685 mmole/l up to and including 1.37 mmole/l; and, the plant having a genome derived only from the genome of the Populus parent hybrid.

* * * * *